United States Patent [19]

Friedli et al.

[11] Patent Number: 4,967,008
[45] Date of Patent: Oct. 30, 1990

[54] POLYAMINES AND THEIR PREPARATION

[75] Inventors: Floyd E. Friedli, Dublin; Robert M. Gilbert, Columbus, both of Ohio

[73] Assignee: Sherex Chemical Company, Inc., Dublin, Ohio

[21] Appl. No.: 464,293

[22] Filed: Jan. 12, 1990

[51] Int. Cl.$^5$ .......................................... C07C 211/14
[52] U.S. Cl. ..................... 564/512; 564/511
[58] Field of Search ........................................ 564/512

[56] References Cited

U.S. PATENT DOCUMENTS 2,246,524  6/1941  Kyrides .............................. 564/512
4,004,030  1/1977  Schwarzmann .................... 564/512

FOREIGN PATENT DOCUMENTS 0025997  4/1981  European Pat. Off. ............ 564/512
0244320  11/1987  European Pat. Off. .

OTHER PUBLICATIONS

Behr, Jean-Paul, "DNA Strongly Binds to Micelles and Vesicles etc." Tetrahedron Letters, vol. 27, No. 48, pp. 5861-5864, 1986.

Primary Examiner—Glennon H. Hollrah
Attorney, Agent, or Firm—Mueller and Smith

[57] ABSTRACT

The present invention is directed to polyamines represented by the following general structure:

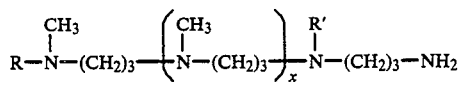

where R is an organic group,
R' is H or CH$_3$, and
x=0—3

Tri, tetra, penta, and hexa amines, accordingly, are disclosed.

The method for making the novel polyamines comprises a multi-step reaction that commences in step (a) with the cyanoethylation of a primary amine, R—NH$_2$, with acrylonitrile under cyanoethylation conditions to form an aminonitrile of the structure R—NH—CH$_2$—CH$_2$—CN. The aminonitrile in step (b) is methylated by reaction with formic acid and formaldehyde under Leuckart reaction conditions to form a monomethyl aminonitrile of the structure R—N(CH$_3$)—CH$_2$—CH$_2$—CN. The monomethyl aminonitrile then in step (c) is reduced, preferably by hydrogenation under hydrogenation conditions, to form a monomethyl diamine of the structure R—N(CH$_3$)—CH$_2$—CH$_2$—CH$_2$—NH$_2$. The monomethyl diamine then in step (d) is chain extended again by cyanoethylation with acrylonitrile under cyanoethylation conditions to form a monomethyl diaminonitrile of the structure R—N(CH$_3$)—CH$_2$—CH$_2$—CH$_2$—NH—CH$_2$—CH$_2$—CN. Finally, the monomethyl diaminonitrile in step (e) is reduced, preferably by hydrogenation under hydrogenation conditions to form the novel polyamine. Repeating step (b) results in R' being a methyl group. Repeating steps (d) and (e) extends x up to 4.

4 Claims, No Drawings

POLYAMINES AND THEIR PREPARATION

BACKGROUND OF THE INVENTION

The present invention relates to polyamines and more particularly to new tri, tetra, penta, and hexa amines and to their synthesis.

Polyamines and polyamides possessing surfactant properties have been shown to be beneficial in a variety of contexts. Asphalt emulsifers and anti-stripping agents are but two of the uses of polyamines that have been proposed in the art. While investigating various amine compositions that might have utility in forming asphaltic compositions, a new class of polyamines and their synthesis was discovered. These new polyamines are terminated at one end with a tertiary amine group and at the other end with a primary amine group. Intermediate amine groups may be secondary or tertiary. Accordingly, a variety of other reactive sites are possessed by the polyamines making them suitable candidates for forming into a variety of derivatives that may find utilty in fields outside of the asphaltic emulsion field. For example, mining ore flotation, epoxy curing agents, and like uses can be contemplated for the novel polyamines and their derivatives.

BROAD STATEMENT OF THE INVENTION

The present invention is directed to polyamines represented by the following general structure:

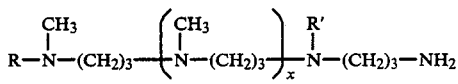

where R is an organic group,
R' is H or CH₃, and
x=0—3
Tri, tetra, penta, and hexa amines, accordingly, are disclosed.

The method for making the novel polyamines comprises a multi-step reaction that commences in step (a) with the cyanoethylation of a primary amine, R—NH₂, with acrylonitrile under cyanoethylation conditions to form an aminonitrile of the structure R—NH—CH₂—CH₂—CN. The aminonitrile in step (b) is methylated by reaction with formic acid and formaldehyde under Leuckart reaction conditions to form a monomethyl aminonitrile of the structure R—N(CH₃)—CH₂—CH₂—CN. The monomethyl aminonitrile then in step (c) is reduced, preferably by hydrogenation under hydrogenation conditions, to form a monomethyl diamine of the structure R—N(CH₃)—CH₂—CH₂—CH₂—NH₂. The monomethyl diamine then in step (d) is chain extended again by cyanoethylation with acrylonitrile under cyanoethylation conditions to form a monomethyl diaminonitrile of the structure R—N(CH₃)—CH₂—CH₂—CH₂—NH—CH₂—CH₂—CN. Finally, the monomethyl diaminonitrile in step (e) is reduced, preferably by hydrogenation under hydrogenation conditions, to form the novel polyamine. Repeating step (b) results in R' being a methyl group. Repeating steps (d) and (e) extends x up to 4.

The novel polyamines additionally may be formed into a variety of derivatives. For example, polyamines may be alkoxylated to form ether linkages or can be reacted with carboxylic acid to form amide groups. Additionally, the polyamines can be epoxidized and can be alkylated to form quaternary ammonium compounds. Thus, a wide variety of polyamine derivatives are subsumed within the present disclosure.

DETAILED DESCRIPTION OF THE INVENTION

The novel polyamines of the present invention are linear and comprise 3-6 amine groups separated by propylene groups. One end is terminated with an organic group while the other end is terminated with a primary amine group. Each of the amine groups commencing with the nitrogen atom bearing the organic group contains a methyl group while the penultimate amine group adjacent the terminal primary amine group may be a secondary amine group or it also can contain a methyl group. The synthesis of the novel polyamines generally commences with a primary amine which is subjected to a cyanoethylation reaction to add a subsequent amine-forming group, i.e. an aminonitrile. The aminonitrile then is subjected to the Leuckart reaction to methylate the amine group. Finally, the nitrile group is reduced to form a terminal amine group. The reaction sequence can be repeated to chain extend the diamine to form a triamine or higher polyamine.

Referring to the initial step of the reaction sequence, a primary amine, R—NH₂, is subjected to a cyanoethylation reaction by addition of acrylonitrile thereto. A wide variety of R substituents are appropriate for the feed primary amine. Organic groups, and especially hydrocarbyl groups ranging from lower alkyl groups on up to long chain fatty groups (e.g. C₈–C₂₂) are advantageous groups upon which to base the novel polyamines. It will be appreciated, however, that the R substituent can be linear or branched in structure and can contain ether groups, amide groups, tertiary amine groups, sulfide and thio groups, and the like. Cyanoethylation is a well-known and practiced reaction involving the reaction of the primary amine with acrylonitrile at elevated temperature ranging from about 25° to 100° C. Details on cyanoethylation are reported in March, *Advanced Organic Chemistry*, 2d Edition, p 679 (McGraw-Hill Book Company, 1977) and Bruson, *Org. React.*, 5, 79–135 (1949). The product of the cyanoethylation reaction is an aminonitrile.

The aminonitrile formed from the cyanoethylation reaction then is subjected to the Leuckart reaction by the addition of formaldehyde and formic acid to the aminonitrile. Organic solvent, e.g. toluene, and other additives (e.g. anti-foam agents) may be used as is necessary or desirable. This methylation reaction is conducted at elevated temperature ranging from about 40° to 150° C. for producing a monomethyl aminonitrile intermediate product. Further details on the Leuckart reaction can be found in March, supra, at pp 819-820.

The monomethyl aminonitrile intermediate then has its nitrile group reduced, preferably by hydrogenation under hydrogenation conditions (e.g. about 50–600 psig) which include the presence of a conventional hydrogenation catalyst, hydrogen gas, and elevated temperature ranging from about 100° to 220° C. Ammonia or other gas may be included for maintaining reducing conditions. Conventional hydrogenation catalysts including nickel, palladium, platinum, copper chromite, and the like are used as is necessary, desirable, or convenient. Raney nickel is a preferred and known catalyst for this reaction. This reduction reaction produces a monomethylated diamine intermediate.

The recovered monomethylated diamine intermediate then can be subjected to the cyanoethylation reaction again to form a monomethylated diaminonitrile. This intermediate then can be reduced for forming a triamine wherein the amino group adjacent the terminal primary amine group is a secondary amine group, or the Leuckart methylation reaction can be conducted again to form a triamine which is dimethylated.

The novel dimethylated triamine then can be chain extended again by use of the cyanoethylation reaction, Leuckart methylation reaction, and reduction reaction in order to produce tetra amines, penta amines, and hexa amines.

The novel polyamines of the present invention should possess excellent coating and surfactant properties and find use in asphaltic compositions as emulsifiers and anti-strip agents, in mining ore flotation, as epoxy curing agents, and like known uses. In this regard, it will be appreciated that a variety of derivatives of the novel polyamines can be synthesized. For example, the polyamines can be alkoxylated utilizing ethylene oxide, propylene oxide, butylene oxide, and higher alkaline oxides to add ether groups and enhance surfactancy. The terminal primary amine group also can be reacted with a carboxylic acid to form an amide. The novel polyamines additionally may be epoxidized to form a Zwitterionic species which then can be alkylated to form a quaternary ammonium salt useful as a curing catalyst for curing polymeric isocyanates, for example. The polyamines additionally can be quaternized directly by the addition of an alkylating agent as is well known in the art. Accordingly, a wide variety of novel polyamine derivatives are included within the present invention.

The following examples show how the present invention has been practiced but should not be construed as limiting. In this application, all units are in the metric system and all percentages and proportions are by weight, unless otherwise expressly indicated. Also, all citations referred to herein are expressly incorporated herein by reference.

IN THE EXAMPLES

EXAMPLE 1

Preparation of N-tallow-N-methyl dipropylene triamine

R—NMe—(CH$_2$)$_3$—NH—(CH$_2$)$_3$—NH$_2$ (a). Tallow primary amine (Adogen 170, 530 g, 2.0 moles, Sherex Chemical Company, Dublin, Ohio) and 5 g water were charged to a round bottom flask fitted with an agitator, additional funnel, and a thermometer. Acrylonitrile (106 g, 2.0 moles) was added slowly over one hour maintaining 50°–60° C. Stirring was continued for another hour at 60° C. Vacuum stripping gave 636 g of amino nitrile.

(b) Methylation of the aminonitrile, from step (a), was done by a modification of the Leuckart reaction. The aminonitrile (636 g, 2.0 moles), toluene (200 g), and antifoam (3 g) were charged to a round bottom flask fitted with an addition funnel, thermometer, agitator, and condenser. A mixture of formaldehyde (37% aqueous, 178 g, 2.2 moles) and formic acid (110 g, 2.4 moles) was added slowly via the addition funnel over 1½ hours maintaining the reaction flask at 95° C. The product mixture was stirred an additional three hours. It was then extracted with hot water three times adding a little salt and isopropanol to aid separation of the layers. The organic layer was vacuum (20-30 mm) stripped at 105° C. to remove volatiles. The resulting product was the desired monomethyl aminonitrile.

(c) Hydrogenation of the methyl amino nitrile was done in a 2 liter stainless steel Parr autoclave using 1% wet Raney nickel at 160° C. with partial pressures of 300 psig ammonia and 300 psig hydrogenation. After hydrogen uptake ceased, the reaction mass was filtered to give the monomethylated diamine which analyzed as:

| Total Amine Value | 292 |
|---|---|
| Secondary/Tertiary Amine Value | 167 |
| Tertiary Amine Value | 113 |

The theoretical amine values are 321, 160 and 160, respectively.

(d) The monomethylated diamine was reacted with another equivalent of acrylonitrile similar to step (a).

(e). Reduction of the acrylonitrile adduct of step (d) by a procedure similar to step (c) gave the desired monomethylated triamine as a liquid which analyzed as:

| Total Amine Value | 381 |
|---|---|
| Secondary/Tertiary Amine Value | 252 |
| Tertiary Amine Value | 134 |

The theoretical values are 415, 276 and 138, respectively.

EXAMPLE 2

Preparation of N-tallow-N,N'-dimethyl dipropylene triamine

R—NMe—(CH$_2$)$_3$—NMe—(CH$_2$)$_3$—NH$_2$

A. The acrylonitrile adduct from step (d) of Example 1 (954 g, 3.0 moles) was methylated via the Leuckart reaction in a manner like that in step (b) of Example 1.

B. The dimethyl adduct, from step A, was hydrogenated to the triamine in a 2 liter stainless Parr reactor fitted with an agitator and cooling coil. 2% wet Raney nickel was the catalyst using partial pressures of 300 psig ammonia and 300 psig hydrogen at 170° C. for seven hours. Filtration gave the desired dimethyl triamine as a liquid.

We claim:

1. A polyamine represented by:

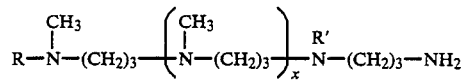

where R is C$_{8-22}$ alkyl
R' is H or CH$_3$, and
x is 0–3.
2. The polyamine of claim 1 wherein R' is H.
3. The polyamine of claim 1 wherein R' is CH$_3$.
4. The polyamine of claim wherein x is 0.

* * * * *